United States Patent [19]
Schmidt

[11] Patent Number: 4,990,256
[45] Date of Patent: Feb. 5, 1991

[54] METHOD, DEVICE AND FILTER MODULE FOR THE FILTRATION OF LIQUIDS IN CROSS-FLOW OPERATION

[75] Inventor: Hans-Weddo Schmidt, Hardegsen, Fed. Rep. of Germany

[73] Assignee: Sartorius AG, Göttingen, Fed. Rep. of Germany

[21] Appl. No.: 350,932

[22] Filed: May 12, 1989

[30] Foreign Application Priority Data

May 13, 1988 [DE] Fed. Rep. of Germany ....... 3816334

[51] Int. Cl.$^5$ .............................................. B01D 65/02
[52] U.S. Cl. .................................... 210/636; 210/350; 210/321.69; 210/409
[58] Field of Search ................ 210/137, 636, 409, 350, 210/251, 321.69, 321.75, 321.84

[56] References Cited

U.S. PATENT DOCUMENTS

| | | | |
|---|---|---|---|
| 3,387,630 | 6/1968 | Routson | 210/350 X |
| 4,374,731 | 2/1983 | Brown et al. | 210/351 X |
| 4,412,553 | 11/1983 | Kopp et al. | 210/137 X |

Primary Examiner—Frank Spear
Attorney, Agent, or Firm—Eric P. Schellin

[57] ABSTRACT

In a method and a device for preventing or breaking down a filter covering layer during the filtration of liquids with finely distributed constitutents therein in a cross-flow operation in which the liquid to be treated is conducted in a narrow overflow slot (SP) between a filter surface (PM) and a slot limiter surface (FM), the slot limiter surface (FM) is brought adhesively into areal contact with the developing filter covering layer (DS) in a periodic manner by means of relative motion relative to the filter surface (PM) and the filter covering layer (DS) is removed in a rinsing fashion from the filter surface (PM) by reactivating the overflow slot (SP) and overflowing the filter surface (PM) and the slot limiter surface (FM). The movable wall is formed by a foil membrane consisting of plastic which is clamped on the edge in a sealing manner in a surrounding housing. The foil membrane can be loaded on the side facing away from the overflow slot by a gas or liquid source and the filter surface (PM) is formed by a flexible, permeable membrane.

24 Claims, 8 Drawing Sheets

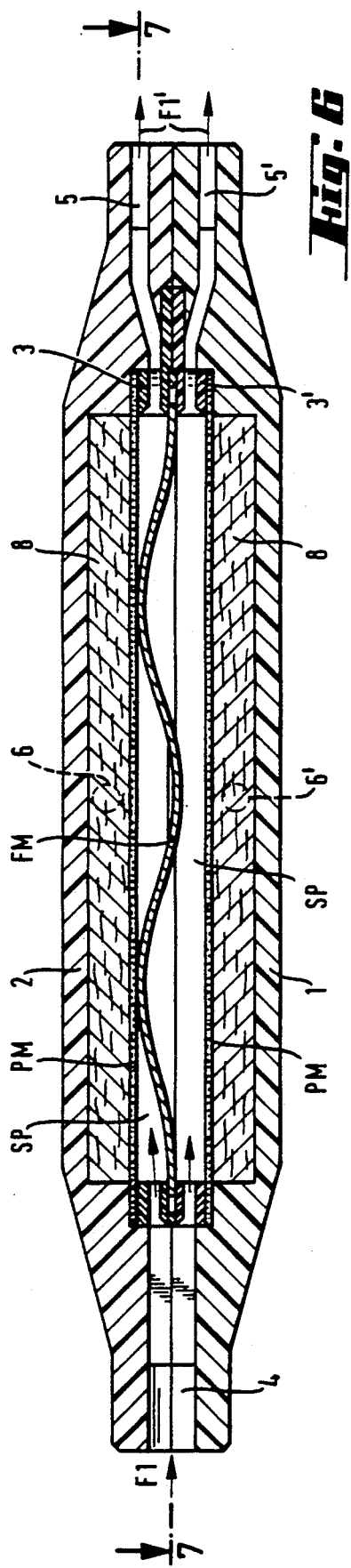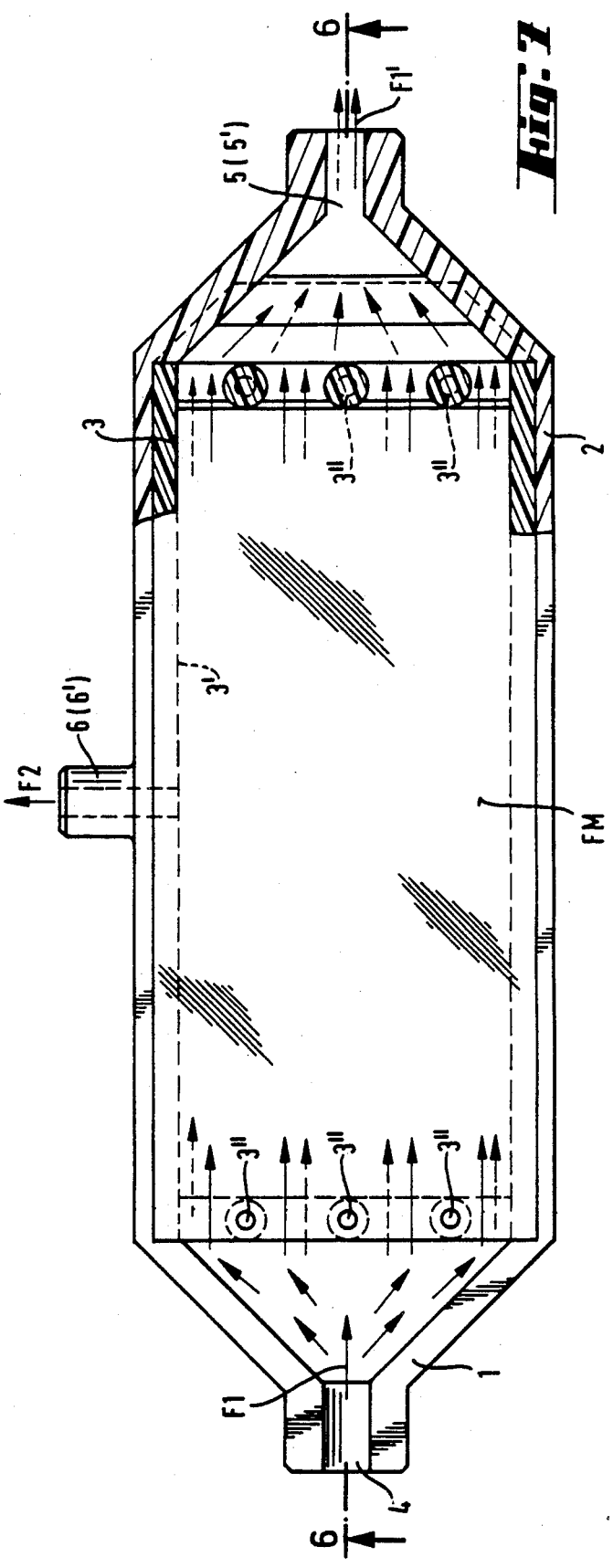

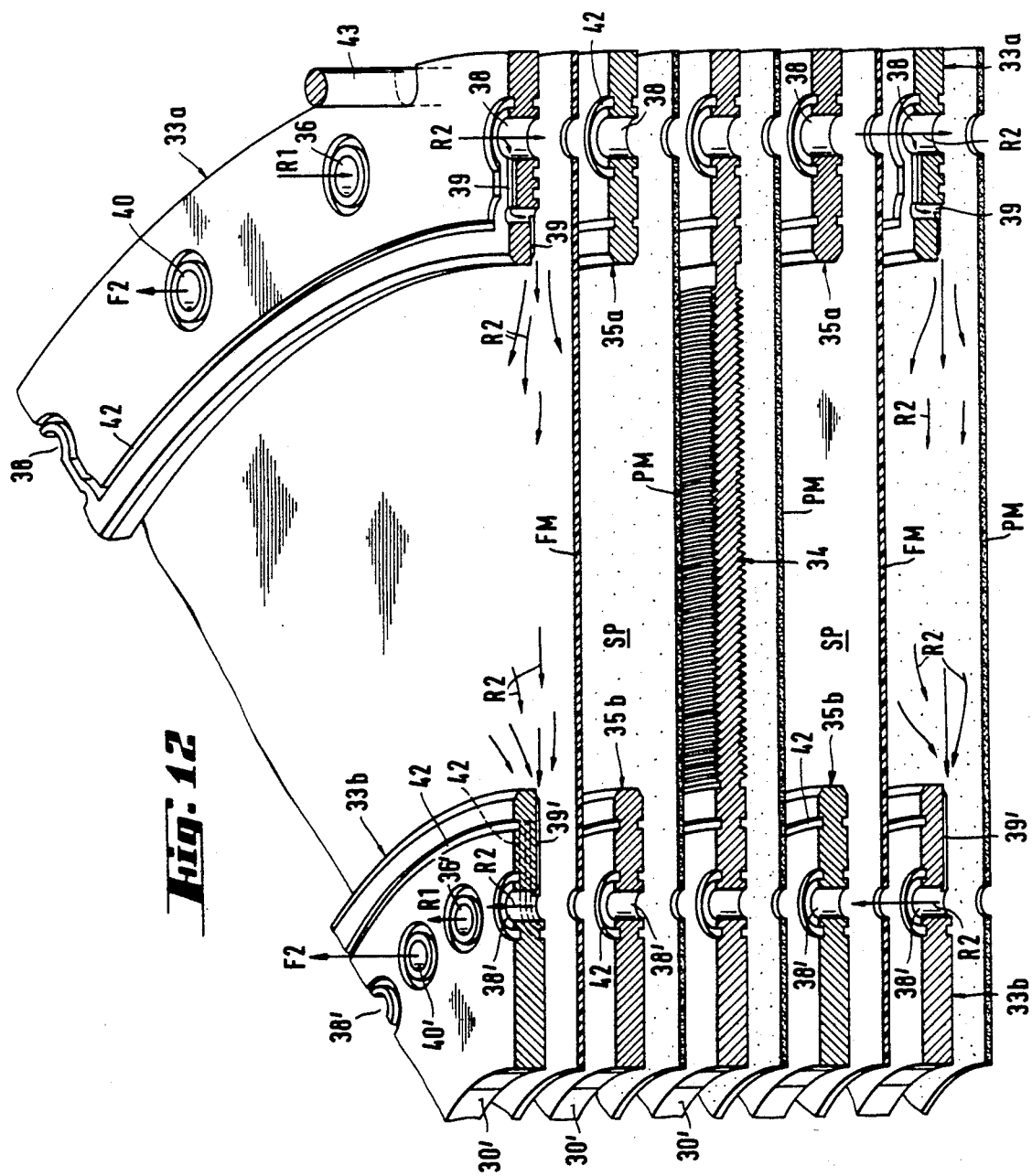

METHOD, DEVICE AND FILTER MODULE FOR THE FILTRATION OF LIQUIDS IN CROSS-FLOW OPERATION

FIELD OF THE INVENTION

The invention relates to a method, a device and a filter module for breaking down or preventing the formation of a filter covering layer during the filtration of liquids with finely distributed constituents therein in a cross-flow operation in which the liquid to be treated is conducted in a narrow overflow slot between a filter surface and a slot limiter impervious to liquid.

BACKGROUND OF THE INVENTION

In a known device for ultrafiltration (DE-OS 26 53 875), the suggestion is made that the slot height be held as small as possible to avoid a formation of a covering layer in order to also keep the developing filter covering layer as small as possible in this manner. This is to be achieved by designing an elastic, impermeable pressure pad between two filter plates with filter medium resting thereupon which pad forms one wall of the slot-shaped filter chamber. The pressure pad should form a pressure-compensation body which is deformed during the flowthrough of the liquid according to the pressure conditions on its surface. This should generate the same local flow resistance over the entire liquid.

It turned out in practice, however, that preferred flowpaths develop in certain areas and the excessive formation of a covering layer can be only partially limited.

It is also customary in filter elements operated according to the cross-flow method (DE-OS 24 41 249) to partially remove a filter covering layer which develops on the microporous filter membrane by loading the filter element from the filtrate side with filtrate or a rinsing agent and subsequently rinsing away the filter covering layer. This has the result that a constant changing must be performed during the actual filtration operation between filtration and backwash with the filtrate already gained and the backwash procedure is only worthwhile during a general cleaning with neutral rinsing agent. In both instances of backwashing, the filter element is therefore also stressed against the actual direction of filtration.

It is also known (DE-OS 34 11 471) that the built-up covering layer in hose filters can be broken down by the hose filters extending freely through the filtrate area and in that their cross section collapses in a reversibly flexible and irregular manner in the case of excess pressure on the filtrate-side. The filter elements are heavily stressed especially by this pulse-like collapsing, which can result in ruptures.

Filtration according to the cross-flow method is becoming more and more significant in the beverage industry. The liquids to be filtered are loaded more or less heavily with finely distributed components. In the filtration of unclarified wines in the cross-flow method, a very rapid and strong covering of the filter membranes with a filter covering layer occurs, even if the attempt is made to delay this flow speeds.

Similar problems occur if a specimen is to be taken from a circulating fermenter broth. The fermenter broth conducted over a filter element in accordance with the cross-flow principle covers the filter membrane very rapidly with a filter covering layer. The fermenter filtrate drawn off on the filtrate side thus frequently does not reflect the actual state of the fermenter broth since the cells from the cell culture contained in the filtrate do not stem from the actual fermenter broth, which is conducted past the covering layer, but rather are old cells or damaged cells which are already located in the filter covering layer.

SUMMARY OF THE INVENTION

The invention therefore solves the problem of making possible the breakdown or the prevention of a filter covering layer during the operation of a filter system according to the cross-flow method with simple means in a manner which protects the filter element.

The invention solves this problem in that the slot limiter is brought adhesively into areal contact with the developing filter covering layer in a periodic manner by means of relative motion relative to the filter surface and the filter covering layer is removed in a rinsing fashion from the filter surface by reactivating the overflow slot and overflowing the filter surface and the slot limiter surface. The externally supplied liquid flow of liquid to be filtered can be periodically interrupted thereby in the overflow slot or the liquid flow is retarded from the outside during the slot-narrowing phase. During the slot-narrowing phase and the renewed slot widening, an elevation of the flow speed occurs according to the venturi tube principle in the slot and during the adhesive, areal contacting of the filter covering layer by the relatively smooth and impervious surface of the slot limiter, the covering layer is separated from the porous filter element so that both effects result in the desired rinsing-off process. The separation of the filter cover layer is all the more intensive, the finer the pores of the surface of the filter element facing the filter covering layer are, so that an especially effective breakdown of the filter covering layer or its prevention can be achieved, in particular when using ultrafilter membranes and microfiltration membranes.

The slot limiter is preferably designed as a fluid-tight foil membrane which can be adjusted on the side facing away from the filter element by supplying liquid into a chamber or by compressed gas or a vacuum for slot formation approximately on the order of 0-1000 $\mu$m. The breakdown of the filter covering layer by turbulence is supported even more if the previously described motions of the membrane and of the flow guidance of the liquid to be treated are performed in a pulsing manner.

Filter elements can be either porous, solid filter elements, e.g. ceramic or glass filters or also flexible filters designed like a membrane, microporous or as relatively dense filter foils for pervaporation.

The impermeable slot limiter can be formed by a movable wall of a housing which surrounds the filter element. The wall can be a plate which can move in a piston-shaped manner but is preferably a foil membrane made of plastic and clamped on its edge in a sealing manner in a surrounding housing.

A quasi-continuous filtration operation is possible via a control device associated with the filtration device using liquid pumps, gas pumps and valves without filtrate which has already been obtained having to be used again by being fed from the filtrate side through the filter membrane into the retentate circuit.

BRIEF DESCRIPTION OF THE DRAWINGS

The concept of the invention will now be explained in several examples of embodiments with reference made to the enclosed drawings.

FIG. 6 schematically shows a vertical section through a rectangular embodiment along line 6—6 in FIG. 7.

FIG. 7 shows a horizontal section along line 7—7 in FIG. 6.

FIG. 12 shows an exploded view similar to that of FIG. 11 along line 12—12 in FIG. 8.

DETAILED DESCRIPTION OF THE INVENTION

Figure 1:
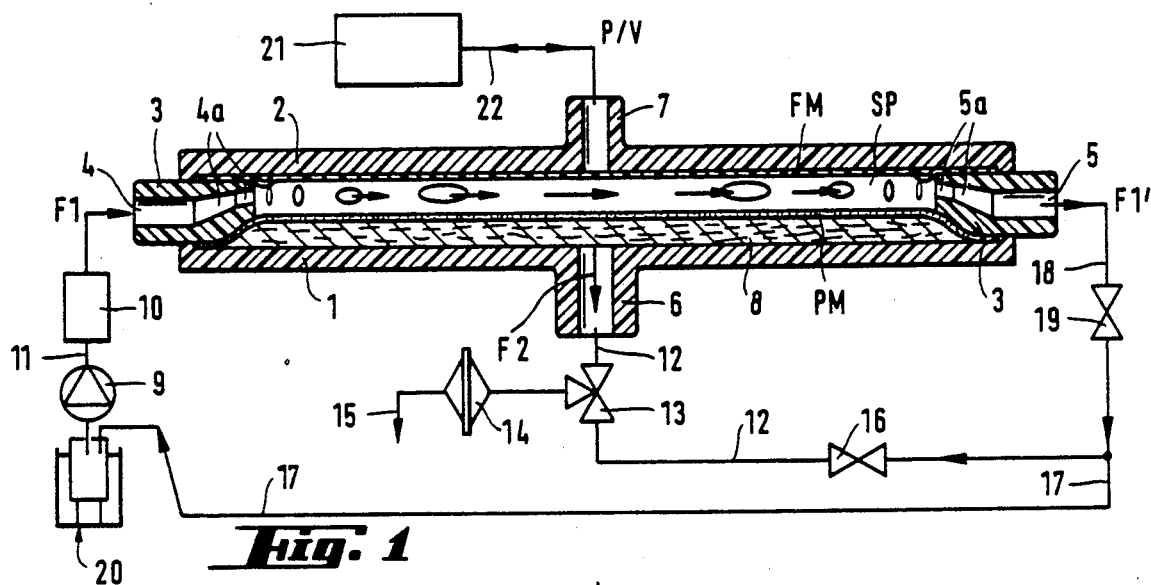
FIGS. 1 to 4 schematically show a cross section through a filter device located in a fermenter circuit as removal device in various filtration phases.

The filter device according to FIGS. 1 to 4 consists of lower housing part 1 with a connection 6 for filtrate, central housing part 3 with diametrically opposite connections 4, 5 for the liquid F1, F1′ to be treated and of upper housing part 2 with a connection 7 for a pressure medium P in the form of gas or liquid or vacuum V. A liquid-tight, smooth foil membrane FM is sealingly clamped in between upper housing part 2 and central housing part 3 on its edges, the back side of which membrane FM can be loaded via connection 7 with fluid and can move parallel to the actual filter surface in the form of a porous membrane PM. This porous membrane PM is located between central housing part 3 and lower housing part 1 and is supported on its bottom, that is, the filtrate side, by an areal, porous drainage layer 8. Both foil membrane FM and porous membrane PM are sealed in a customary manner by circumferential sealing rings or by welding opposite the housing parts 1 to 3 in order to form separate fluid chambers. A relative narrow overflow slot SP is formed between both membranes FM and PM which slot can be adjusted in accordance with the invention by loading foil membrane FM on the order of 0–1000 μm during the filtration operation.

The filter device is a part of a specimen removal device for a fermenter 20. To this end, connection 4 for the liquid F1 to be treated, here fermenter broth via line 11, non-return valve 10 and pump 9 are connected to fermenter 20. Connection 5 for the non-concentrated or concentrated fermenter broth F1′ is also connected to fermenter 20 via line 18, valve 19 and line 17 in the circuit. Connection 6 for filtrate F2, a three-way valve 13, line 12 and a valve 16 are likewise connected to line 17 running to fermenter 20. A specimen-removal position for fermenter filtrate is formed via three-way valve 13 via bypass line 15 with sterile filter 14 located between them. Pressure-vacuum supplier 21 furnishes connection 7 either with liquid or gaseous pressure medium P/V via line 22.

Figure 2:
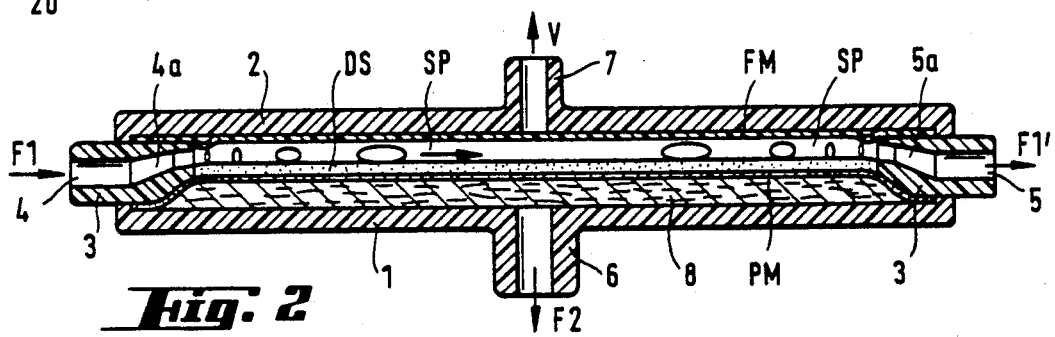
Figure 3:
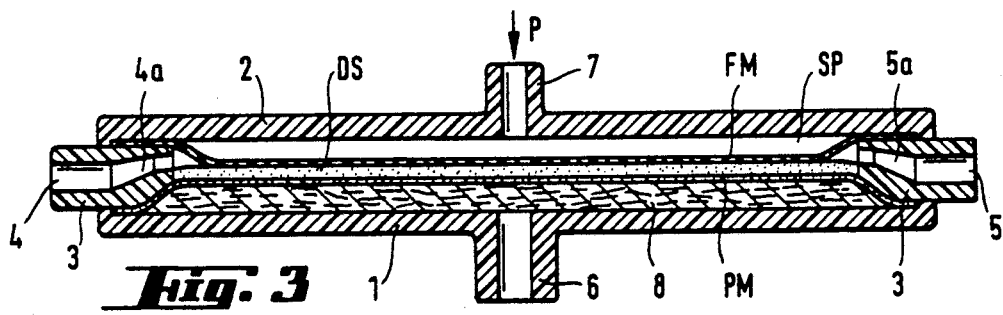
Figure 4:
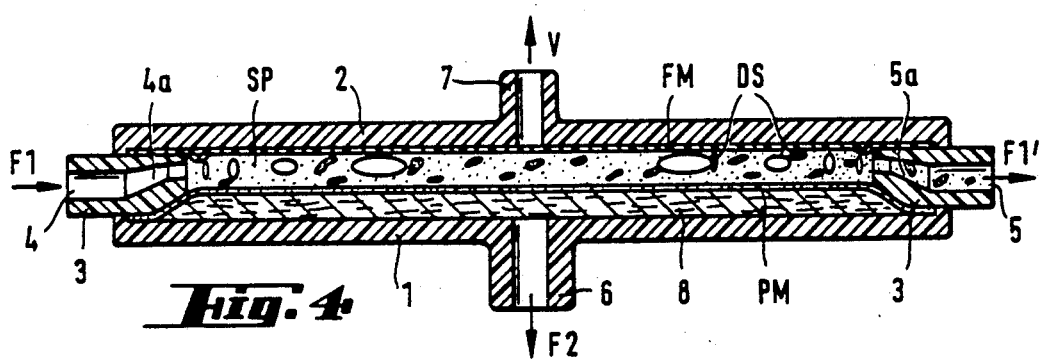

As soon as a filter covering layer DS has developed during the filtration operation or also during the pure overflow without removal of filtrate in overflow slot SP in the setting according to FIG. 1 or also in a narrower setting therebetween approximately according to FIG. 3, overflow slot SP is periodically constricted according to FIG. 2 to such an extent by loading foil membrane FM that the latter comes in adhesive, areal contact according to FIG. 3 with the surface of filter covering layer DS. The adhesive forces between relatively smooth foil membrane FM and filter covering layer DS result at a subsequent widening of overflow slot SP in a breakdown of the boundary surface of filter covering layer DS and therewith in a dissolution of the cross-sectional structure so that the filter covering layer DS dissolved by liquid F1 flowing through the constricted overflow slot SP according to the principle of a venturi conduit at an elevated flow speed in overflow slot SP is flushed back into the fermenter circuit according to FIG. 4. The motion of flexible foil membrane FM which occurs during the rinsing overflow supports the dissolution of filter covering layer DS so that the latter is removed except for residue in the pores, depending on the pore size of porous membrane PM or of a rigid filter medium.

Draining filter support 8 is advantageously held very tightly in the form of grooves and/or formed by an areal support fleece so that no corrugated elevations and depressions are formed on porous membrane PM and thus overflow slot SP is formed by two limitations running parallel to one another.

Porous membrane PM can be kept free of a filter covering layer by means of the pulsating loading of foil membrane FM in coordination with the flow guidance of liquid F1, F1′ and F2 so that when a specimen is removed from removal position 15, the actual fermenter filtrate can be removed. To this end, only valve 16 in line 12 is closed. The removal is therefore performed without sensitive cell cultures having to penetrate a damaging filter covering layer DS.

Figure 5:
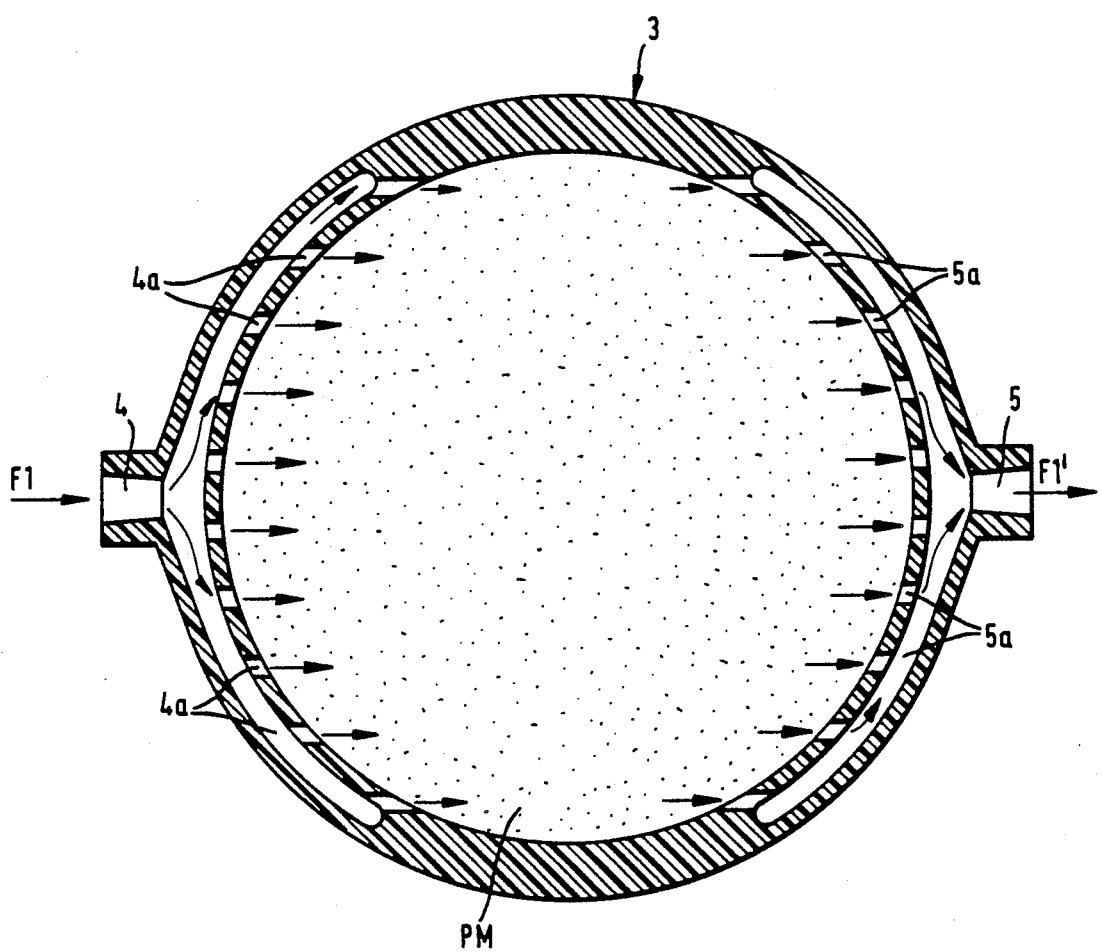
FIGS. 5 shows a schematically simplified horizontal section through the central housing part of the filter device according to FIGS. 1 to 4.

FIG. 5 shows a section through central housing part 3 for the essentially circular filter device in a schematically simplified fashion. Connections 4, 5 merge thereby into a plurality of distributor conduits 4a and connector conduits 5a.

In the embodiment according to FIGS. 6 and 7, the movable wall forms a flow divider in the form of foil membrane FM which divides the overflow slot into two partical slots, over which membrane FM the flow can pass on both sides and which can move between walls (porous membranes PM) limiting the overflow slot. Foil membrane FM is circumferentially clamped in between housing parts 1, 2, 3, 3′, whereby the overflow in the two partial slots can take place in parallel fashion or, given an additional connection 4, in countercurrent. Foil membrane FM pulses on account of its excess size and flexibility and optionally its extensibility at a maximum between the two limiting slot walls PM. Foil membrane FM can consist e.g. of silicon, be fixed like a punched card by pins 3″ in central housing part 3, 3′ at the inlet and outlet 4, 5 and clamped in on the other side edges.

If the overflow chamber is designed to be rectangular, it is sufficient if foil membrane FM is clamped in on two opposite sides as a flow divider in housing 1 to 3, whereby the foil length between the clamped-in areas is maintained somewhat greater than the distance between the clamping areas so that the foil can also move in a pulsing manner here between boundary positions. The states and positions of foil membrane FM between its limitation walls PM can be influenced by closing of throttle valves at connections 4, 5, 5', 6, 6'.

It is also possible to clamp a rectangular foil in a rectangular overflow chamber only on the end facing the approach side as a flow divider. The foil, which flaps like a flag in a free-moving fashion with its other end in the overflow slot prevents the formation of a covering layer therewith.

In the embodiment according to FIGS. 8 to 12, circular individual elements are stacked on a lower end plate around a central clamp bolt 30 connected thereto and are covered by another, upper end plate with fluid connections which plate is guided on clamp bolt 30 and is pressed by tension means against the stack of individual elements, whereby fixing elements 43' and 43 are provided on clamp bolt 30 and/or on the periphery of the circular individual elements which fixing elements assure that the perforations in the stack which extend through the individual elements are in alignment and correspond in the proper sequence in the circumferential direction. In the embodiment described in the following, foil membrane FM is located between two porous membranes PM with interpositioning of spacing frames 33a, 33b and 35a, 35b and the loading with pressure of foil membrane FM in the direction of the one or of the other porous membrane take place with the aid of the liquid to be treated, so that the latter is designated for the sake of a better distinction by retetante R1 and retentate R2.

Figure 8:
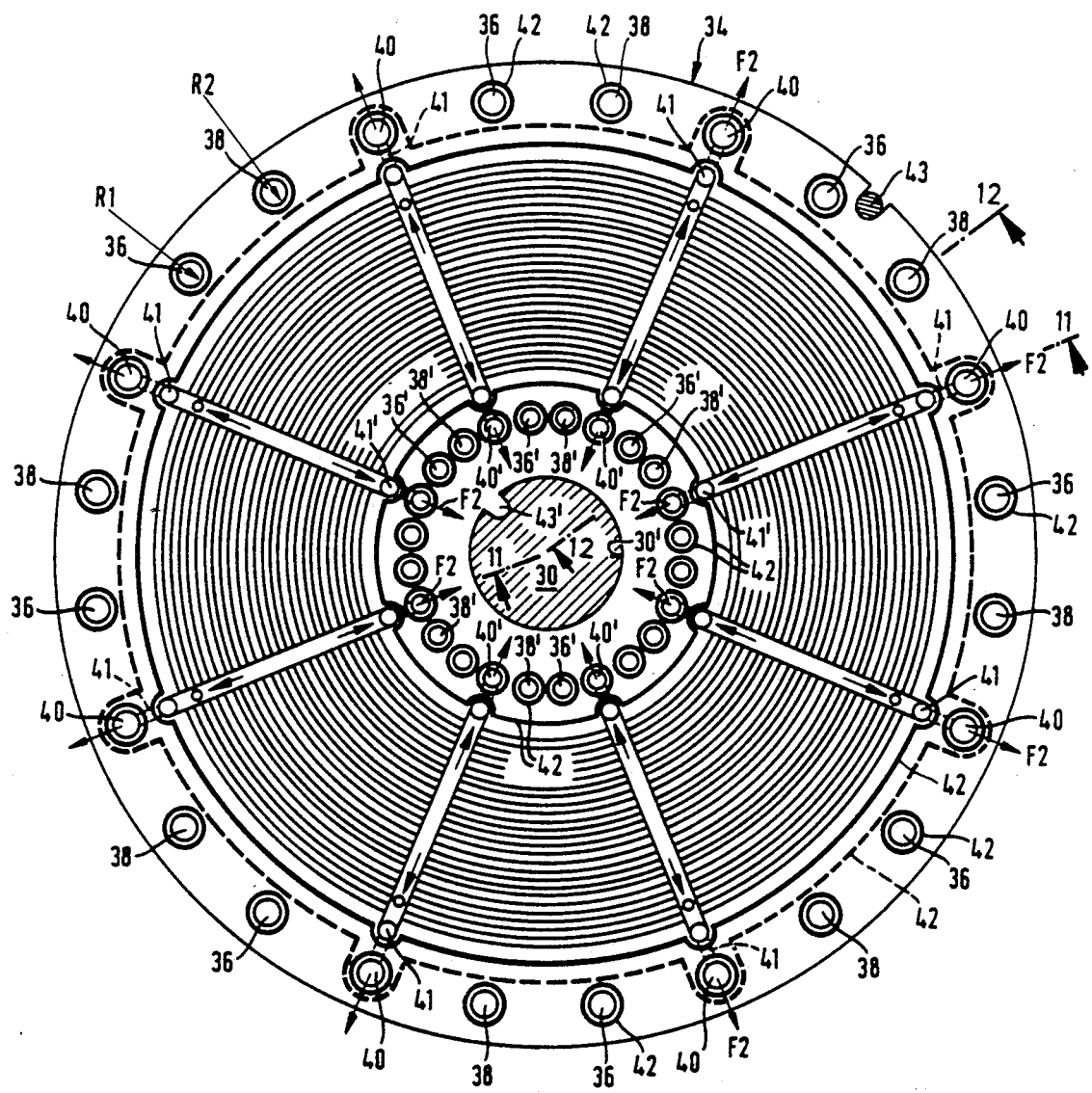
FIG. 8 shows a top view of the filtrate plate for a round, stacked filter module.
Figure 9:
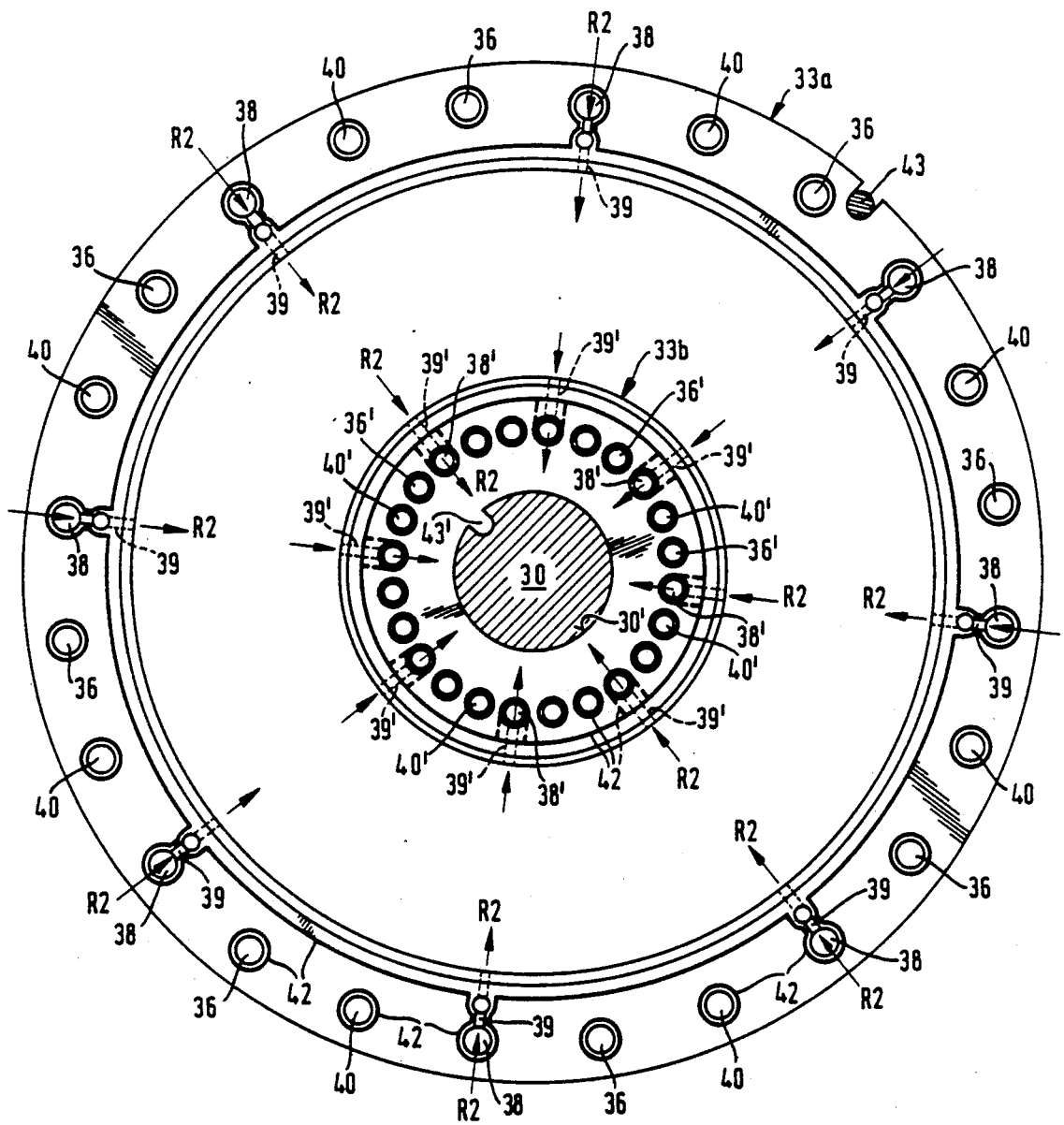
FIGS. 9 and 10 show a top view of spacing plates.
Figure 10:
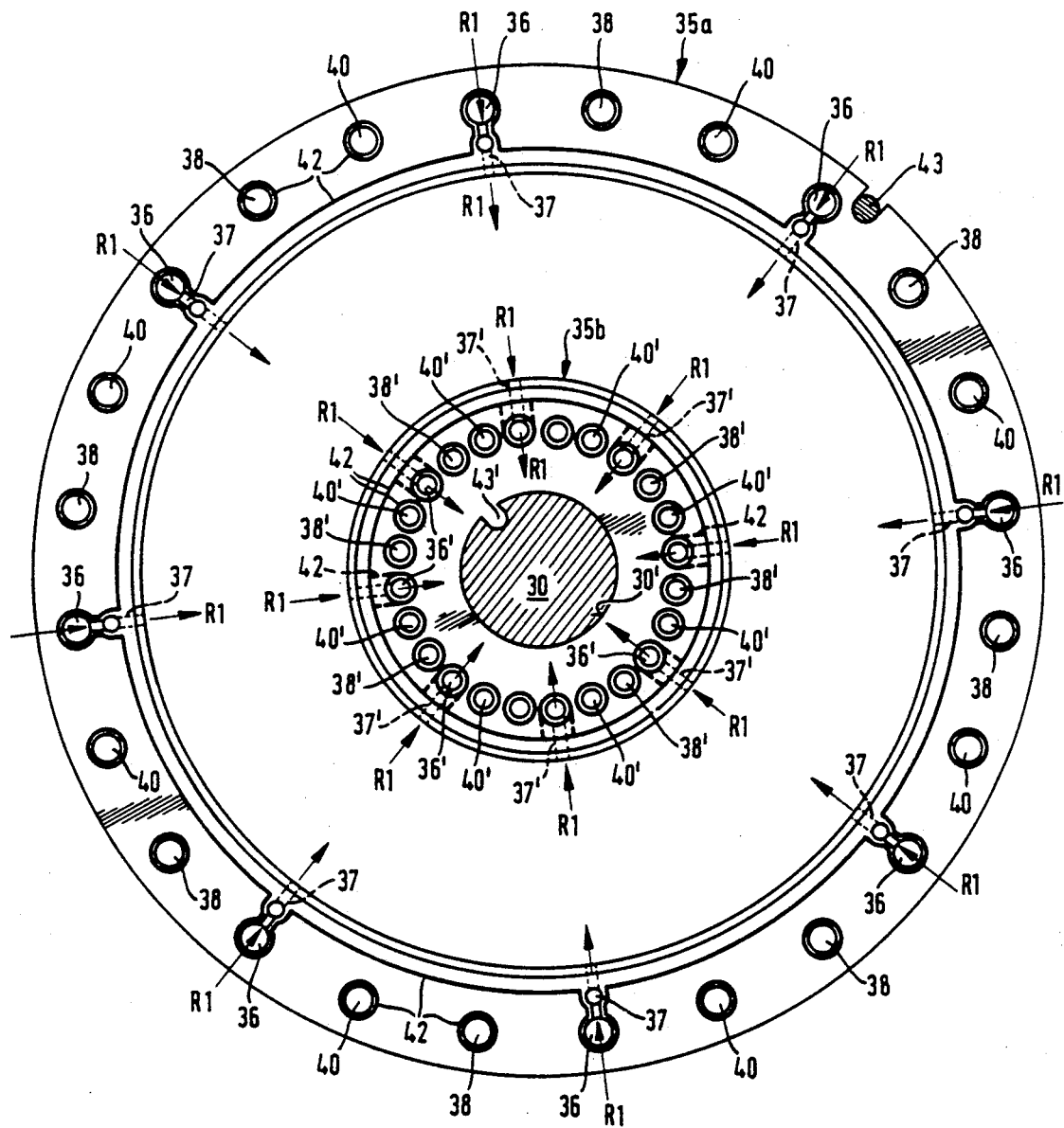

Filtrate support 34 according to FIG. 8 and visible in a detailed edge section in FIGS. 9, 10 comprises perforations 36 distributed over the circumference on the outer edge and perforations 36' on the inner edge for the introduction and removal of retentate R1, corresponding perforations 38, 38' for the introduction and removal of retentate R2, perforations 40, 40' and connection conduits 41, 41' for the removal of filtrate F2, whereby the perforations are entirely or partially surrounded by sealing elements 42. Filtrate support plate 34 comprises a plurality of concentrially arranged ribs and conduits as well as radial draining conduits so that a level support surface for porous membrane PM is formed in accordance with FIGS. 9 to 12.

Figure 11:
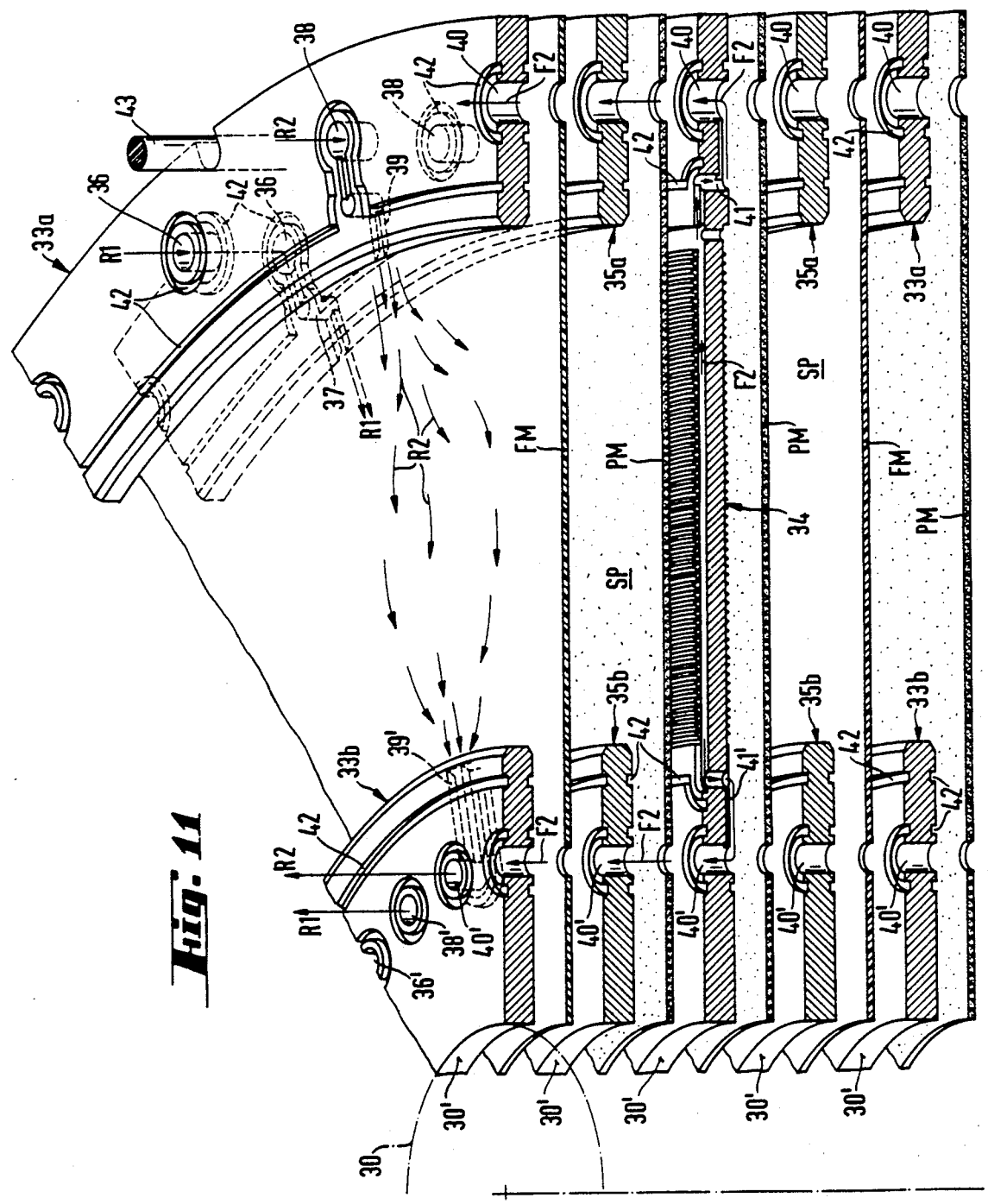
FIG. 11 shows a perspective vertical section through the stacked filter module along section line 11—11 in FIG. 8 in an exploded view.

Filtrate support plate 34 is covered according to FIGS. 11, 12 on both sides by a porous membrane PM which extends up to the outer edge and to the inner edge 30' (FIG. 8).

The two porous membranes PM are separated by inner (35b) and outer (35a) spacing frames from a correspondingly dimensioned foil membrane FM and the latter from a further, adjacent, porous membrane PM by a further type of inner (33b) and outer (33a) spacing frames with connection conduits 39, 39' at perforations 38, 38' for guiding retentate R2. The first type of spacing frame 35a, 35b also comprises connection conduits 37, 37' for guiding retentate R1 in perforations 36, 36'. Perforations 36, 36', 38, 38' and 40, 30' extend through all elements, that is, spacing frames 33, 35, 33a, 33b, 35a, 35b, foil membranes FM, filtrate support plate 34 and porous membrane PM and, optionally, through at least one end plate.

In the embodiment shown, support plates 34 and spacing frames 33a, 33b, 35a, 35b are either thin metal plates or thin plastic plates. In the first instance, sealing elements 42 including the remaining profiling are manufacted in the form of grooves, connection conduits are perforations in an etching process. The geometry of the flow guidance can be simplified by the selection of different manufacturing techniques, e.g. by means of simple radial conduits and apertures. Both foil membrane FM as well as porous membrane PM are sealed by groove-shaped sealing elements 42 and by contact pressure and swelling in this area.

The method described in conjunction with the schematic embodiment according to FIGS. 1 to 4 for preventing or breaking down a filter covering layer takes place in that the simultaneous inflow of retentate R1 and R2 into perforations 36, 38 is reduced in an alternating and periodic manner so that e.g. the foil membrane FM shown uppermost in FIGS. 11, 12 moves downward at an increase in pressure of R2 and at a reduction of pressure of R1 and contacts porous membrane PM and the filter covering layer. As a result of an increase in pressure in R1 and reduction of pressure in R2, the same foil membrane FM moves in the direction of an oppositely located, porous membrane, which is not shown in FIGS. 11, 12, with corresponding filter support plate 34. This causes the filter covering layer to be loosened from the first porous membrane PM and rinsed away while the filtering overflow of the oppositely located, porous membrane PM takes place by means of retentate current R2 and via perforations 38, 38' and connection conduits 39, 39'.

A quasi-continuous filtration operation is possible by means of an appropriate controlling of the pulsation.

It is of course possible to feed in a separate pressure medium in the form of a liquid or a gas instead of the loading with pressure by means of retentate R1 and R2 themselves. It is only necessary to this end that each two foil membranes FM are spaced from each other by an inner and an outer spacing frame 35a, 35b and 33a, 33b and that these special flow chambers are sealed off from the retentate chambers and filtrate chambers. The control of the fluid currents takes place via control devices and control valves.

The fluid introduced between two foil membranes FM for a pulsing motion of the two foil membranes can also be a heat-exchanger medium in order to be able to temper the liquids to be filtered as required.

The previously described method has the advantage that the covering layer or the filter cake is broken down as rapidly as possible or its creation can be directly eliminated since the latter is no longer subject to aging and thus can no longer harden. It is especially advantageous that said filtration unit does not require a large pump output and the energy claimed acts directly on the filter membrane. The invention avoids a constantly alternating stress on the filter elements due to alternating filtration operation and backwash, as occurs in known methods of breaking down a covering layer.

What is claimed is:

1. A method for preventing or breaking down a developing filter covering layer (DS) during the filtration of liquids with finely distributed constituents therein a cross-flow operation comprising the steps of
    conducting liquid to be treated in a narrow overflow slot (SP) between a filter surface (PM) and an impermeable, flat slot limiter surface (FM),
    periodically disposing the slot limiter surface (FM) adhesively into areal contact with the developing filter covering layer (DS) or with the filter surface (PM) by means of relative motion relative to the filter surface (PM), and
    removing the filter covering layer (DS) in a rinsing fashion from the filter surface (PM) by reactivating the overflow slot (SP) and overflowing the filter surface (PM) and the slot limiter surface (FM).

2. The method according to claim 1, wherein the flow of liquid in the overflow slot is periodically interrupted.

3. The method according to claim 1, wherein the flow of liquid in the overflow slot is retarded during the slot constriction phase.

4. A device for preventing or breaking down a developing filter covering layer (DS) during the filtration of liquids with finely distributed constituents therein in a cross-flow operation comprising
means conducting liquid (F1) to be treated in a narrow overflow slot (SP) between a filter surface (PM) and a parallel slot limiter surface (FM) which is impermeable to liquid, and
the slot limiter surface (FM) and the filter surface (PM) can be moved relatively toward one another until contact with the filter covering layer (DS) developing in the overflow slot (SP) on the filter surface (PM) or until contact with the filter surface (PM) and can be removed from one another again.

5. The device according to claim 4, wherein the slot limiter surface is formed by a movable wall of a housing which surrounds the filter surface.

6. The device according to claim 5, wherein the movable wall is formed by a plate which can move in a piston-shaped manner.

7. The device according to claim 5, wherein the movable wall is formed by a foil membrane consisting of plastic which is clamped in on the edge in a sealing manner in the surrounding housing.

8. The device according to claim 7, wherein the foil membrane on the side facing away from the overflow slot can be loaded by a gas source or a liquid source.

9. The filter module according to claim 8, wherein the overflow chamber is constructed to be rectangular and that a rectangular vibratable foil is clamped in the housing only on the end facing the approach side as a flow divider with an end in a free-moving fashion in the overflow slow.

10. The filter module according to claim 8, wherein the movable wall forms a flow divider in the form of a foil, over both sides of which the flow can pass, which is optionally extensible, which divides the overflow slot into two partial slots and which can move between walls of the filter elements limiting the overflow slot.

11. The filter module according to claim 10, wherein the overflow chamber is constructed to be rectangular and that a rectangular foil is clamped in the housing only on the ends facing the approach side and the trailing side as a flow divider, whereby the foil length between the clamping points is maintained somewhat greater than the distance between the clamping points.

12. The device according to claim 4, wherein the filter surface is formed by a flexible, porous membrane.

13. The device according to claim 12, wherein the porous membrane is supported on the filtrate side in an areally draining fashion.

14. The device according to claim 12, wherein the porous membrane is an ultrafiltration membrane.

15. The device according to claim 12, wherein the porous membrane is a microfiltration membrane.

16. The device according to claim 4, wherein the filter surface is formed by a permeable pervaporation membrane.

17. A filter module for the filtration of liquids with components finely distributed therein in cross-flow operation comprising
a permeable filter membrane which is enclosed on the edge in a sealing manner in a surrounding housing with connections (4, 5, 6) between housing parts (1, 2, 3),
the filter membrane forming an overflow surface on one side for the liquid to be treated and forming a draining surface on the other side for removing the filtrate,
the overflow surface of the permeable membrane being covered approximately parallel thereto by a slot limiter means, and
the slot limiter means being formed by a flexible foil membrane which is held on the edge on housing parts (2, 3) and is mobile to a limited extent in its distance from the overflow surface of the permeable membrane on the side facing away from the overflow surface by means of pressure medium.

18. The filter module according to claim 17, wherein circumferential spacing frames (33a, 33b, 35a, 35b) limiting the overflow slot are located between the permeable membranes clamped in on the edge between housing parts and are located between the foil membranes, which spacing frames comprise flow conduits (35 ... 40 and 36', 38', 40') for the flow guidance.

19. The filter module according to claim 18, wherein a draining support plate with flow conduits (36, 38, 40, 41, 36', 38', 40', 41') is located between tow permeable membranes.

20. The filter module according to claim 19, wherein circumferential spacing frames (33a, 33b, 35a, 35b) limiting the overflow slot are located between two foil membranes.

21. The filter module according to claim 20, wherein several permeable membranes, foil membranes, spacing frames (33a, 33b, 35a, 35b) and draining filter support plates (34) stacked on each other to a unit forming flow chambers are sealingly connected and their flow conduits (36, 38, 40, 41, 36', 38', 40', 41') can be loaded via lines with fluid.

22. The filter module according to claim 21, wherein the stacked unit forming the flow chambers is arranged around a central clamp bolt (30) and that the stacked unit is covered on both ends by end plates, at least one of which is guided on the clamp bolt (30) in a movable fashion and at least one of which comprises the lead connections for supplying the fluid chambers.

23. The device according to claim 17, wherein the association of a control device (9 ... 22) for the coordinated guidance of the currents of liquid, the slot constriction and the slot enlargement.

24. The device according to claim 7, wherein the association of a control device (9 ... 22) for the coordinated guidance of the currents of liquid, the slot constriction and the slot enlargement as well as for the removal of filtrate specimens from a closed circuit of liquid, especially a fermenter circuit.

* * * * *